(12) United States Patent
Yoshida et al.

(10) Patent No.: US 6,238,530 B1
(45) Date of Patent: May 29, 2001

(54) CATHODE FOR ELECTROLYSIS AND ELECTROLYTIC CELL USING THE SAME

(75) Inventors: Yasuki Yoshida; Masashi Tanaka; Setsuro Ogata, all of Kanagawa; Hiroshi Inoue; Chiaki Iwakura, both of Osaka, all of (JP)

(73) Assignee: Permelec Electrode Ltd., Kanagawa (JP)

( * ) Notice: Subject to any disclaimer, the term of this patent is extended or adjusted under 35 U.S.C. 154(b) by 0 days.

(21) Appl. No.: 09/503,228

(22) Filed: Feb. 11, 2000

(30) Foreign Application Priority Data

Feb. 15, 1999 (JP) .................................................. 11-036109

(51) Int. Cl.[7] ...................................................... C25B 9/00
(52) U.S. Cl. .......................... 204/252; 204/266; 204/283; 204/290.08; 204/290.14; 204/293
(58) Field of Search ..................................... 204/252, 256, 204/258, 266, 278, 283, 290.08, 290.14, 293; 205/616, 637, 638, 639

(56) References Cited

U.S. PATENT DOCUMENTS

| | | | |
|---|---|---|---|
| 4,832,805 | * | 5/1989 | LaConti et al. ....................... 204/283 |
| 5,494,560 | * | 2/1996 | Arimoto et al. ................. 204/290.08 |
| 5,954,928 | * | 9/1999 | Kishi et al. ...................... 204/290.08 |

* cited by examiner

Primary Examiner—Bruce F. Bell
(74) Attorney, Agent, or Firm—Sughrue, Mion, Zinn, Macpeak & Seas, PLLC

(57) ABSTRACT

A cathode for electrolysis comprising a hydrogen-occluding material for use in an electrolytic cell partitioned by the cathode into two chambers including a reaction chamber and an electrolysis chamber. The cell is arranged so that a reactant is reduced or hydrogenated in the reaction chamber. The cathode comprises an ion exchange membrane or porous membrane. A first layer made of a hydrogen-occluding metallic palladium or a palladium alloy is formed on the reaction chamber side of the membrane. A second layer which is a porous catalyst layer made of a platinum metal black or gold is formed on the first layer. Also disclosed is an electrolytic cell using the cathode for electrolysis.

13 Claims, 1 Drawing Sheet

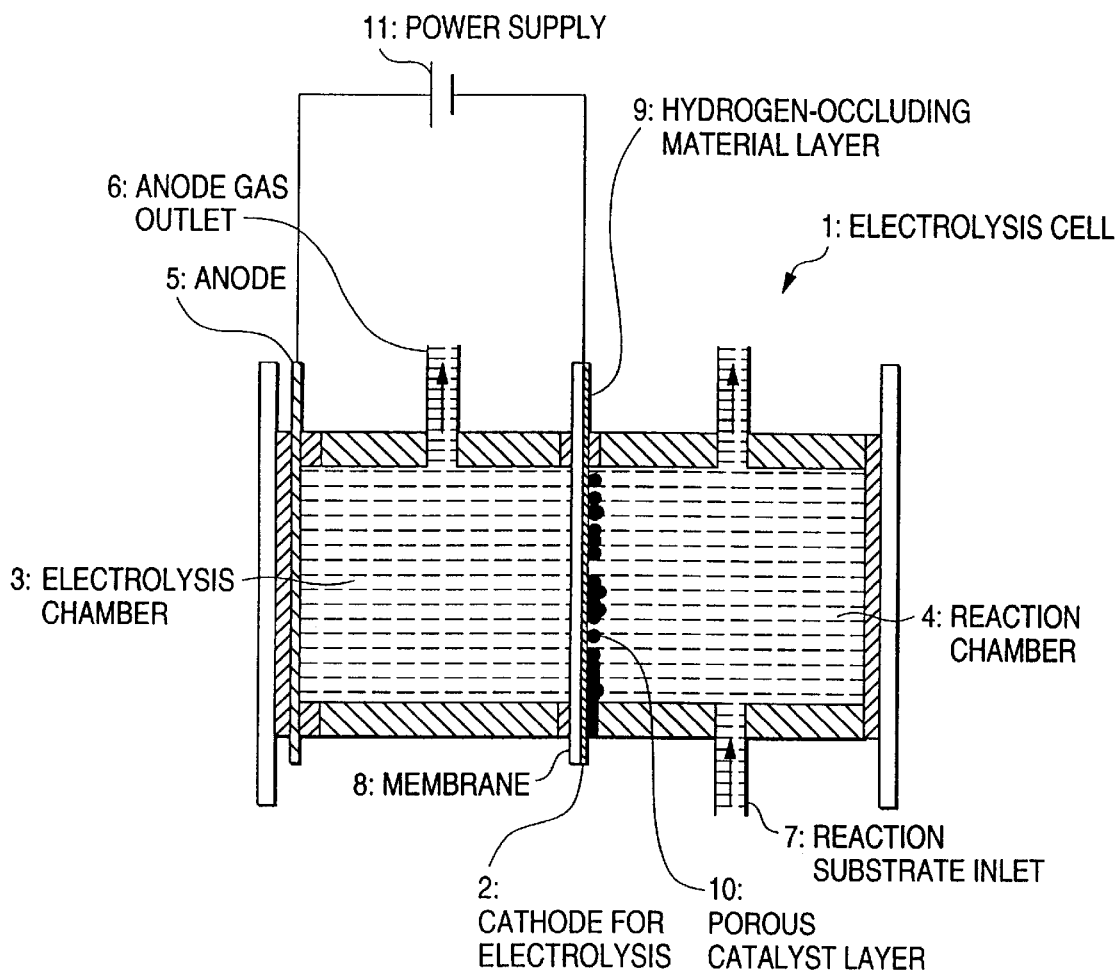

CATHODE FOR ELECTROLYSIS AND ELECTROLYTIC CELL USING THE SAME

FIELD OF THE INVENTION

The present invention relates to a cathode for electrolysis providing for efficient, continuous and inexpensive hydrogenation/reduction utilizing hydrogen produced by electrolysis and an electrolytic cell using the same.

BACKGROUND OF THE INVENTION

The hydrogenation reaction of organic compounds has been used in a variety of chemical arts. For example, the cracking reaction of petroleum involves the hydrogenation of heavy oil to gasoline or kerosine. Some hydrogenation reactions have been put to practical use. For example, tar is hydrogenated to a liquid so that it is more suitable for further applications. Furthermore, hydrogenation is used to convert unsaturated hydrocarbon to a corresponding saturated hydrocarbon.

This hydrogenation reaction normally proceeds in a uniform system. For example, an organic compound is reacted in the presence of a contact catalyst in a reaction cell while supplying hydrogen. A noble metal such as palladium is known as an excellent catalyst for the hydrogenation of unsaturated hydrocarbon (S. Siegel, "Comprehensive Organic Synthesis", ed., B. M. Trost and I. Fleming, Pergamon Press, Oxford, 1991, vol. 8). This hydrogenation reaction uses high pressure hydrogen and thus requires the use of a high pressure vessel. Further, this hydrogenation reaction mostly takes place at a relatively high temperature. Moreover, this hydrogenation reaction is disadvantageous in that the hydrogen that is used may explode depending on its purity. This hydrogenation reaction is also disadvantageous in that the catalyst has an insufficient reaction selectivity, causing the production of by-products.

In order to enhance the reaction selectivity and reduce the consumption of energy, an electrolytic reduction method involving a nonuniform reaction has been employed as described in A. M. Couper, D. Pletcher and F. C. Walsh, "Chem. Rev.", 1990, [90], 837, T. Nonaka, M. Takahashi and T. Fuchigami, "Bull. Chem. Soc. Jpn.", 183 [56], 2584, M. A. Casadei and D. Pletcher, "Electrochim. Acta", [33], 117 (1988), T. Yamada, T. Osa and T. Matsue, "Chem. Lette,", 1989 (1987), L. Coche, B. Ehui, and J. C. Moutet, "J. Org. Chem.", [55], 5905 (1990), and J. C. Moutet, Y. Ouennoughi, A. Ourari and S. Hamar-Thibault, "Electrochim. Acta", [40], 1827 (1995).

The use of an electrode catalyst having a large surface area such as a Raney nickel catalyst allows for an electrochemical hydrogenation reaction. Thus, good power efficiency can be expected. Further, operation can be effected easily and safely. However, in order for the organic reaction to proceed electrolytically, the organic compound itself must be electrically conductive. Otherwise, additives must be added to render the electrolyte containing an organic compound electrically conductive. Since most organic compounds are nonconductive, the addition of additives to the organic compounds complicates the reaction system to disadvantage. Further, the addition of additives not only complicates the operation but also adds to the level of impurities.

It is known that in hydrogenation reactions the atomic hydrogen produced on the catalyst acts to accelerate the reaction regardless of whether the catalyst is uniform or nonuniform.

Another conventional method for effecting a hydrogenation reaction efficiently and safely comprises supporting hydrogen on palladium or another hydrogen-occluded alloy and contacting the same with a reactant to be hydrogenated (K. Ohkawa, K. Hashimoto, A. Fujishima, Y. Noguchi and S. Nakayama, "J. Electroanal. Chem.", [345], 445 (1993)). Palladium and most of the above hydrogen-occluding alloys exhibit catalytic action in these reactions. Hydrogen in palladium or other hydrogen-occluding metals acts as an active hydrogen having strong reactivity. It is thus considered that palladium or the like acts as a hydrogen source and a hydrogenation catalyst to exhibit high performance in the hydrogenation of organic compounds. However, since the amount of hydrogen which can be occluded in these alloys is limited, the hydrogenation reaction in the presence of palladium or a hydrogen-occluding alloy no longer proceeds as the occluded hydrogen is used up, leaving part of the organic compound unreacted. Therefore, such a hydrogenation reaction must be carried out batchwise. This batchwise hydrogenation reaction brings about no problem on a laboratory basis. However, this discontinuous operation is extremely inefficient on an industrial scale.

In order to overcome these difficulties, the present inventors proposed an electrolytic method comprising conducting electrolysis in an electrolytic cell comprising an anode and a cathode made of a hydrogen-occluding material. The reactant is in contact with the side of the cathode opposite the anode and atomic hydrogen produced on the cathode is occluded by the cathode. The reactant is hydrogenated by atomic hydrogen which permeates through the cathode to the side opposite the anode (JP-A-9-184080). However, the arrangement comprising as a partition a metal plate such as palladium is disadvantageous in that palladium or the like is expensive. A metal foil, if any, is disadvantageous in that it can easily break if used over a large area.

SUMMARY OF THE INVENTION

It is therefore one object of the present invention to provide an inexpensive cathode for electrolysis which is suitable for use on a large scale by forming a partition comprising a plate of a metal such as palladium from a material having a high strength which cannot break. It is also an object of the present invention to provide a cathode having a large area and which is capable of occluding hydrogen atom produced thereon and which allows hydrogen atoms to permeate therethrough to the side of the cathode opposite the anode.

The above objects of the present invention are achieved by providing a cathode for electrolysis comprising an ion exchange membrane or porous membrane, a first layer comprising a hydrogen-occluding metallic palladium or palladium alloy formed on at least a reaction chamber side of the membrane, and a second layer which is a porous catalyst layer comprising a platinum metal black or gold formed on said first layer.

It is another object of the present invention to provide an electrolytic cell employing the above cathodes, partitioned by said cathode into two chambers including a reaction chamber and an electrolysis chamber, the cell being adapted for subjecting a reactant to reduction or hydrogenation in said reaction chamber, wherein said cathode comprises an ion exchange membrane or porous membrane.

The above objects of the present invention are also achieved by providing an electrolysis chamber, wherein an electrolysis chamber contains a gas outlet and reaction chamber comprising an inlet and an outlet for passing a reactant through the reaction chamber.

BRIEF DESCRIPTION OF THE DRAWING

By way of example and to make the description more clear, reference is made to the accompanying drawing in which:

The FIGURE is a schematic diagram illustrating an electrolytic cell comprising an electrolysis chamber and a reaction chamber defined by a cathode for electrolysis, wherein the reference numeral 1 indicates an electrolysis cell, the reference numeral 2 indicates a cathode for electrolysis, the reference numeral 3 indicates an electrolysis chamber, the reference numeral 4 indicates a reaction chamber, the reference numeral 5 indicates an anode, the reference numeral 6 indicates an anode gas outlet, the reference numeral 7 indicates a reaction substrate inlet, the reference numeral 8 indicates a membrane, the reference numeral 9 indicates a hydrogen-occluding material layer, the reference numeral 10 indicates a porous catalyst layer, and the reference numeral 11 indicates a power supply.

DETAILED DESCRIPTION OF THE INVENTION

Embodiments of the present invention will be described hereinafter, but the present invention should not be construed as being limited thereto.

The structure of an apparatus according to the invention is shown in FIG. 1. An electrolytic cell 1 is partitioned by a cathode 2 for electrolysis into an electrolysis chamber 3 and a reaction chamber 4. The cathode 2 for electrolysis (hereinafter also referred to simply as "cathode") comprises a hydrogen-occluding material layer 9 made of palladium or a palladium alloy as a first layer formed on one side of a membrane 8 made of ion exchange membrane or porous membrane and a porous catalyst layer 10 made of a platinum metal black or gold as a second layer supported thereon.

The ion exchange membrane for use as the membrane 8 may be selected from a cation exchange membrane and an anion exchange membrane. From an economic standpoint, NAFION 117 (available from Du Pont) is desirable. Referring to the porous membrane, polyethylene, polyester and polypropylene membranes are commercially available as neutral separating membranes from YUASA IONICS CO., LTD. and NAKAO FILTER MEDIA CO., LTD. The membrane is appropriately selected depending on the desired pore diameter and properties.

Referring next to the first layer made of palladium or a palladium alloy (hydrogen-occluding material layer), a process for forming such a hydrogen-occluding material layer on an ionically dissociative ion exchange membrane is preferably an adsorption reduction method as disclosed in JP-B-58-47471. In accordance with this method, a uniform thin palladium layer having a thickness of from 0.1 $\mu$m to 5 $\mu$m is formed as a subbing layer. The thin palladium layer is then plated with palladium by an electroless plating method so that a thin palladium layer is formed to a desired thickness. The electroless plating solution may be, e.g., LECTROLESS PD1000 (available from Nihon Electroplating Engineers Co., Ltd.). Further, the formation of the first layer made of palladium or a palladium alloy on the porous membrane can effectively be accomplished by a physical film-forming method such as vacuum evaporation, sputtering and ion plating and an electroless plating method in combination.

When the first layer is formed on the porous membrane, the interior of the porous membrane can also be plated. Accordingly, it is effective to form the first layer not only on one side of the porous membrane but also on both sides thereof. Namely, it is desirable to fill the pores of the porous membrane with palladium or a palladium alloy so as to allow atomic hydrogen to permeate from the electrolysis chamber through the cathode and into the reaction chamber.

The thickness of the first layer made of palladium or a palladium alloy is preferably from 0.5 to 40 $\mu$m. The first layer is provided on only one side of the ion exchange membrane or porous membrane which serves as a partition. The partition is then positioned such that the first layer faces the reaction chamber 4. A porous catalyst layer 10 is then supported as a second layer on the first layer to enhance the hydrogenation reaction rate. The second layer has a thickness of from 0.5 to 40 $\mu$m. This arrangement forms the cathode 2. The metal incorporated in the second layer is a catalyst that takes part in the hydrogenation reaction. Specific examples of the catalyst include platinum group metals such as palladium, platinum, gold, iridium, ruthenium, rhodium and silver.

For the hydrogenation reaction, a catalyst which can easily be provided with a large surface area so as to increase contact with the reactant is preferably used. From this viewpoint, a platinum metal black or gold, particularly palladium black or platinum black, is desirable. Most preferred among these catalytic materials is palladium black, which has no gloss. This is because palladium black has a large surface area and can form a catalyst layer having an extremely excellent performance as a reduction catalyst, particularly for organic compounds. Further, palladium is capable of occluding and releasing hydrogen in addition to its catalytic capability to advantage. Where an inorganic compound is the substance to be reacted, it is also effective to support a metal such as copper, nickel, zinc, gold and silver on palladium black in addition to the noble metal.

The electrolysis chamber 3 is filled with an aqueous solution of sulfuric acid or an electrolytic solution containing an electrolyte such as sodium hydroxide. The cathode 2 is connected to a power supply 11. The electrolysis chamber 3 comprises an insoluble anode 5 disposed on the side thereof opposite the cathode 2. The anode 5 is made of platinum. In practice, however, a so-called insoluble electrode may be used instead of platinum. In order to lower the cell voltage, a porous anode may be disposed close to the partition or in close contact with the partition, if it is an ion exchange membrane support. The reference numeral 6 indicates an anode gas outlet which may be provided with an electrolytic solution supply port. When the electrolysis cell is energized by the power supply 11 applied between the anode 5 and the cathode 2, hydrogen produced by electrolysis in the electrolysis chamber 3 is occluded by palladium in the cathode 2. The hydrogen permeates through the cathode 2 into the reaction chamber 4 where it then contacts the substance to be hydrogenated to thereby proceed with the hydrogenation reaction. During this procedure, the porous catalyst layer 10 formed on the reaction chamber side of the cathode 2 accelerates the hydrogenation reaction.

The substance to be hydrogenated may either be an inorganic compound or an organic compound. Any inorganic or organic compound without particular limitation can be subjected to hydrogenation reduction in accordance with the invention whether it is liquid or gaseous. Thus, no supporting electrolyte is required.

When the electrolytic aqueous solution is subjected to electrolysis between the cathode 2 having a porous catalyst layer formed thereon and the anode 5 in the electrolysis chamber 3, hydrogen is produced on the palladium or palladium alloy layer formed on the cathode 2. Thus, hydrogen atom is produced.

$$H^+ + e^- \rightarrow H_{ad} \tag{1}$$

The hydrogen atom thus produced is adsorbed by the surface of the palladium or palladium alloy layer formed on the cathode 2, and then occluded deeply into the palladium or palladium alloy layer of the cathode 2 without being desorbed.

$$H_{ad} \rightarrow H_{ab} \quad (2)$$

wherein $H_{ad}$ represents adsorbed hydrogen, and $H_{ab}$ represents absorbed hydrogen. The hydrogen atom which has been occluded deep into the palladium or palladium alloy layer of the cathode 2 then diffuses through the palladium or palladium alloy layer to the porous catalyst layer 10 where it is adsorbed but readily desorbed on the inner side of the reaction chamber 4. When the hydrogen atom which has thus been adsorbed and occluded contacts the substance to be hydrogenated, the hydrogenation reaction proceeds.

The electrolytic current density for hydrogenation is preferably such that the production of hydrogen gas on the surface of the porous catalyst layer 10 cannot be observed. Specifically, it is preferably from 0.1 to 10 A/dm², more preferably from 1 to 5 A/dm². When the electrolytic current density falls below 0.1 A/dm², the reaction disadvantageously takes too long. Finally, the electrolytic current density can be selected by the concentration of the substance to be hydrogenated.

The present invention will be further described in the following examples, but the present invention should not be construed as being limited thereto.

EXAMPLE 1

An ion exchange membrane NAFION (trade name) 117 (available from Du Pont) which had been roughened by abrading with a sand paper having a #800 or like mesh was processed in boiling 2N Hcl for 30 minutes, washed with water, and then subjected to the following processing to support palladium on only one side thereof.

Adsorption bath
  Palladium chloride: 1 g/λ
  28% Aqueous ammonia: 80 ml/λ
  Temperature: 60° C.
  Time: 2 hours
Reduction bath
  Sodium borohydride: 1 g/λ
  28% Aqueous ammonia: 80 ml/λ
  Temperature: 60° C.
  Time: 2 hours.

In this manner, a palladium layer was formed at a thickness of 7 μm calculated in terms of layer thickness. The electrode thus formed was then disposed as a partition/cathode 2 in the central portion of the electrolysis cell 1. A platinum plate having a thickness of 1 mm was then disposed in the electrolysis chamber 3 as an anode 5 opposite the cathode 2. The electrolysis chamber 3 was filled with a 1 mol/λ aqueous solution of sulfuric acid. The reaction chamber 4 was charged with styrene as a react ion substrate. Styrene was then hydrogenated by energizing the electrolysis chamber 3 under the following conditions:

Anode: Platinum
  Cathode: NAFION (trade name) 117 (effective area: 2 cm²) having palladium supported thereon to a thickness of 7 μm
  Current density: 3 A/dm²
  Temperature: Room temperature
  Reaction substrate: Styrene (purity: 100%) (volume: 30 ml)

As a result, the current efficiency with respect to the hydrogenation of styrene was 32%.

EXAMPLE 2

The hydrogenation of styrene was conducted in the same manner as in Example 1, except that palladium was disposed on both sides of the NAFION (trade name) 117 membrane. As a result, the current efficiency with respect to the hydrogenation of styrene was 11%.

EXAMPLE 3

Palladium was supported on one side of a NAFION (trade name) 117 membrane to a thickness of 7 μm in the same manner as in Example 1. Thereafter, using a commercially available electroless palladium plating solution, palladium was further deposited on the palladium-bearing side of the substrate to a thickness of 3 μm.

Thereafter, using a cathode having palladium black further supported on the palladium-bearing side of the substrate to a thickness of 15 μm, the hydrogenation of styrene was conducted under the same conditions as used in Example 1. As a result, the current efficiency with respect to the hydrogenation of styrene was 100%. This means that all hydrogen atoms produced by electrolysis contributed to the hydrogenation of styrene.

Comparative Example 1

The hydrogenation of styrene was conducted in the same manner as in Example 2, except that a commercially available palladium foil having a thickness of 50 μm was used as a cathode. As a result, the current efficiency with respect to the hydrogenation of styrene was 89%.

EXAMPLE 4

A thin palladium layer was formed on one side of a neutral membrane (available from YUASA IONICS CO., LTD.) to a thickness of 0.1 μm by vacuum evaporation. Using a commercially available electroless palladium plating solution, palladium was further supported on the side of the membrane bearing the thin palladium layer to a thickness of 10 μm. Thereafter, using a cathode having palladium black further supported on the palladium-bearing side of the membrane to a thickness of 10 μm, the hydrogenation of styrene was conducted under the same conditions as used in Example 1. As a result, the current efficiency with respect to the hydrogenation of styrene was 95%.

EXAMPLE 5

An electrode was prepared in the same manner as in Example 2. Thereafter, nickel was supported on the electrode to a thickness of 0.1 μm, and the reduction of nitric acid ion was conducted under the following conditions:

Anode: Platinum
  Cathode: NAFION (trade name) 117 (effective area: 2 cm²) having palladium black (thickness of 10 μm) and nickel (thickness of 0.1 μm) supported on a palladium layer having a thickness of 10 μm
  Electrolytic solution: 1 mol/λ sulfuric acid
  Current density: 1 A/cm²
  Reaction substrate: 0.01 mol/λ sodium nitrate solution (30 ml)
  Temperature: Room temperature As a result, nitric acid ion was completely reduced at a current efficiency of about 60%.

Comparative Example 2

The reduction of nitric acid ion was conducted under the same conditions as used in Example 4, except that nickel was not provided on the electrode. As a result, nitric acid ion was not reduced at all.

In accordance with the present invention, by forming a metal layer made of a hydrogen-occluding material on an ion exchange membrane or porous membrane as a support, and then forming a catalyst layer thereon, an inexpensive cathode for electrolysis which cannot break when used over a large area and which is suitable for use on a large scale can be obtained.

Further, the present invention provides a process which comprises conducting electrolysis with a cathode comprising a hydrogen-occluding metal member to produce hydrogen which is occluded by the surface of the cathode. The occluded hydrogen permeates at least a part of the opposite side of the hydrogen-occluding metal member where it is then desorbed to cause a continuous hydrogenation reaction. The present invention also provides an apparatus therefor. The cathode is characterized in that the hydrogen-occluding metal member comprises a porous catalyst layer provided on the surface thereof. The catalyst layer accelerates the reaction of hydrogen desorbed from the hydrogen-occluding metal membrane with the reactant. Further, because the catalyst layer is porous, the area at which the reactant and hydrogen come in contact with each other is increased, making it possible to raise the reaction rate. Accordingly, even if electrolysis is effected at an increased current density to produce hydrogen at an increased rate, the hydrogenation reaction rate can be maintained with this enhancement, making it possible to obtain a high current density and hence increased hydrogenation or reduction efficiency.

While the invention has been described in detail and with reference to specific embodiments thereof, it will be apparent to one skilled in the art that various changes and modifications can be made therein without departing from the spirit and scope thereof.

What is claimed is:

1. A cathode for electrolysis comprising a hydrogen-occluding material for use in an electrolytic cell partitioned by said cathode into two chambers including a reaction chamber and an electrolysis chamber, the cell being adapted for subjecting a reactant to reduction or hydrogenation in said reaction chamber, wherein said cathode comprises an ion exchange membrane or porous membrane, a first layer comprising a hydrogen-occluding metallic palladium or palladium alloy formed on at least the reaction chamber side of the membrane, and a second layer which is a porous catalyst layer comprising a platinum metal black or gold formed on said first layer.

2. The cathode for electrolysis as claimed in claim 1, wherein said first layer comprises a metallic palladium or palladium alloy layer formed by vacuum evaporation, sputtering or ion plating.

3. The cathode for electrolysis as claimed in claim 1, wherein said first layer has a thickness of from 0.5 to 40 $\mu$m.

4. The cathode for electrolysis as claimed in claim 1, wherein said second layer has a thickness of from 0.5 to 40 $\mu$m.

5. The cathode for electrolysis as claimed in claim 1, further comprising a noble metal or a metal selected from the group consisting of copper, nickel, zinc and silver supported on the second layer of the cathode as a hydrogenation or reduction catalyst.

6. An electrolytic cell comprising an anode and a cathode comprising a hydrogen-occluding material, said cathode partitioning said electrolytic cell into an electrolysis chamber and a reaction chamber, whereby atomic hydrogen produced on said cathode by electrolysis in said electrolysis chamber is occluded by said cathode and then permeates through said cathode to reduce or hydrogenate a reactant in said reaction chamber, wherein said cathode comprises an ion exchange membrane or porous membrane, a first layer comprising a hydrogen-occluding metallic palladium or palladium alloy formed on at least the reaction chamber side of the membrane, and a second layer which is a porous catalyst layer comprising a platinum metal black or gold formed on said first layer.

7. A cathode for electrolysis comprising an ion exchange membrane or a porous membrane, a first layer comprising a hydrogen-occluding metallic palladium or palladium alloy formed on one side of the membrane, and a second layer which is a porous catalyst layer comprising a platinum metal black or gold formed on said first layer.

8. The cathode as claimed in claim 7, wherein said membrane is a porous membrane having pores, and said hydrogen-occluding metallic palladium or palladium alloy of the first layer fills the pores of the porous membrane.

9. The cathode as claimed in claim 7, wherein said first and second layers are only present on the reaction chamber side of the membrane.

10. An electrolytic cell comprising a cathode partitioning said cell into an electrolysis chamber containing an anode and a reaction chamber, wherein said cathode comprises an ion exchange membrane or porous membrane, a first layer comprising a hydrogen-occluding metallic palladium or palladium alloy formed on the reaction chamber side of the membrane, and a second layer which is a porous catalyst layer comprising a platinum metal black or gold formed on said first layer.

11. The electrolytic cell as claimed in claim 10, wherein said membrane is a porous membrane having pores, and said hydrogen-occluding metallic palladium or palladium alloy of the first layer fills the pores of said porous membrane.

12. The electrolytic cell as claimed in claim 10, wherein said first and second layers are only present on the reaction chamber side of the membrane.

13. The electrolytic chamber of claim 10, wherein said electrolysis chamber further comprises a gas outlet, and said reaction chamber comprises an inlet and an outlet for passing a reactant through said reaction chamber.

* * * * *